Dec. 24, 1963 W. P. MORGAN Plant Pat. 2,331
ROSE PLANT
Filed Dec. 13, 1962
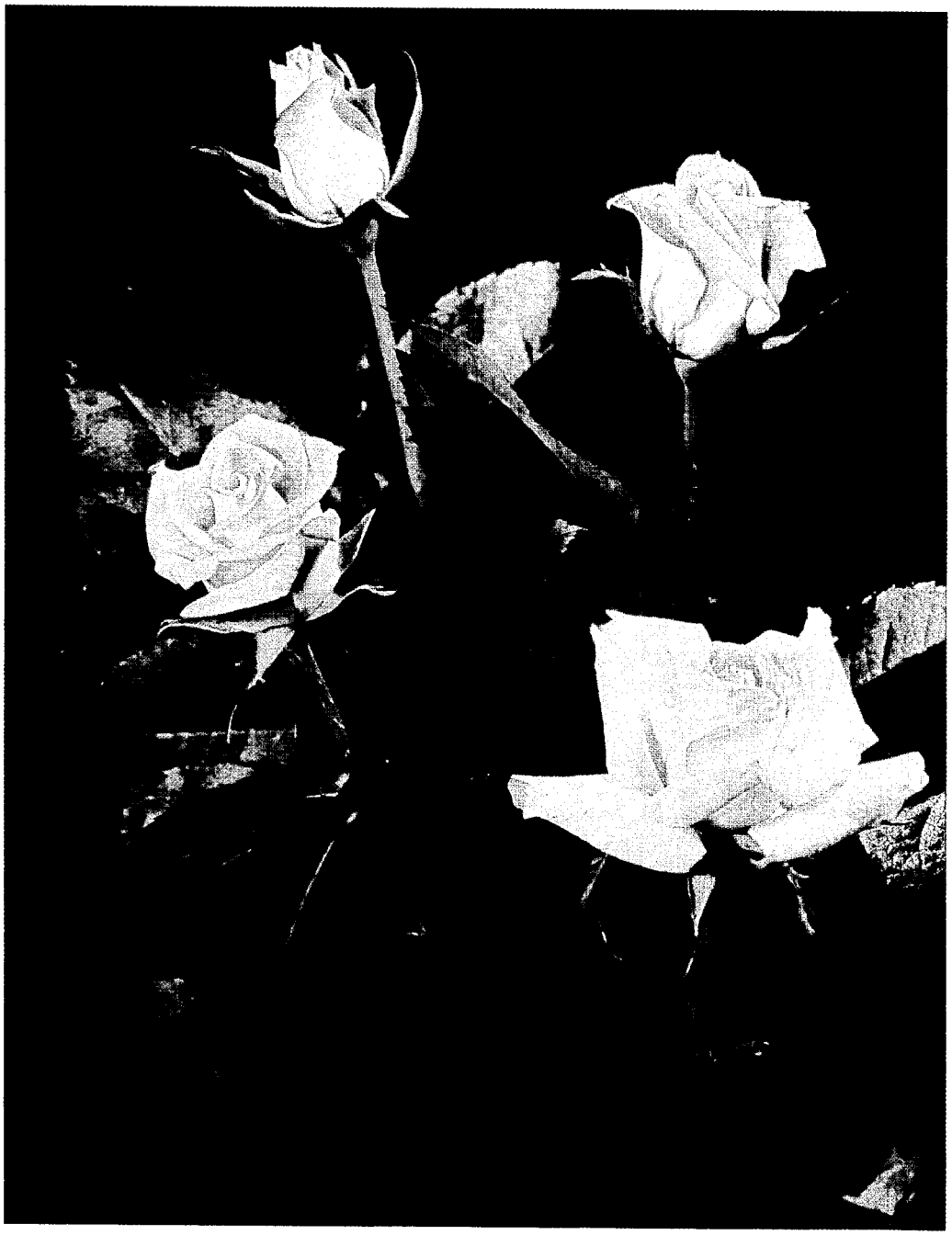
Inventor.
William P. Morgan
By: Robb & Robb
Attorneys.

United States Patent Office

Plant Pat. 2,331
Patented Dec. 24, 1963

2,331
ROSE PLANT

William P. Morgan, Indianapolis, Ind., assignor to Carlton Rose Nurseries, Carlton, Oreg., a corporation of Oregon Filed Dec. 13, 1962, Ser. No. 244,536
1 Claim. (Cl. Plt.—22)

The present invention relates to a new and distinct variety of rose plant of the floribunda class, which was originated by me by crossing the variety known as "Little Darling" (Plant Patent No. 1,581) with an unnamed and unpatented seedling derivated from a cross of "Red Pinocchio" (Plant Patent No. 812) × "Masquerade" (Plant Patent No. 975).

As the result of this breeding, I have produced a new rose variety which is endowed with the following unique combination of characteristics which are outstanding in the new variety and which distinguish the same from its parents, as well as from all other varieties of which I am aware:

(1) Strong and healthy habits of growth;

(2) Numerous, upright and strong stems of medium length;

(3) Large, shiny, thick, luxurious and rich dark green foliage which is borne on the plant from the ground up to near the flowers;

(4) Abundant flower production;

(5) Distinctive and attractive flower buds of buff white color, tipped with Crimson over about ¼ of the outer ends of the petals, said buds gradually opening to present a Crimson irradiance when viewed by looking into the open flowers, and said flowers being of very good quality and having the ability to hold their shape and color for an extended period of time; and (6) A suitability for both commercial cut flower production and for garden decoration.

Asexual reproduction of my new variety by budding, as performed at Gaston, Oregon, and Carlton, Oregon, shows that the foregoing characteristics and distinctions come true to form and are established and transmitted through succeeding propagations.

The accompanying drawing shows typical specimens of the flowers and foliage of my new variety in different stages of development, and as depicted in color as nearly true as it is reasonably possible to make the same in a color illustration of this character.

The following is a detailed description of the new variety, with color terminology in accordance with the Horticultural Colour Chart issued by the British Colour Council in collaboration with The Royal Horticultural Society, except where general color terms of ordinary dictionary significance are obvious:

Type: Hardy; bush; greenhouse and outdoor; for cut flowers and for garden decoration.

Class: Floribunda.

Breeding: Seedling.

*Seed parent.*—"Little Darling."

*Pollen parent.*—An unnamed seedling of "Red Pinocchio × "Masquerade."

Propagation: Holds its distinguishing characteristics through succeeding propagations by budding.

*Flower*

Locality where grown and observed: Carlton, Oregon.

Continuity: Continuous.

Fragrance: Moderate. Nature—sweetbriar.

Flowers borne: Singly; on strong stems of medium length.

Quantity of bloom: Abundant, both outdoors and in greenhouse.

Bud:

*Peduncle.*—Short; medium heavy; erect; stiff; almost smooth; few prickles. Color—medium green.

*Before calyx breaks.*—Size—medium. Form—medium pointed; without a conspicuous neck; with foliaceous appendages on the surface of the bud; with much-cut foliaceous parts extending beyond the tip of the bud equal to ½ of its length. Color—Scheele's Green, Plate 860/1.

*As calyx breaks.*—Color—creamy white, corresponding to Naples Yellow, Plate 403/3.

*As first petal opens.*—Size—medium. Form—pointed. Color: outside—between Naples Yellow, Plate 403 and Naples Yellow, Plate 403/2 from base to about ¾ of distance to tip, then gradually fusing to margin of Tyrian Rose, Plate 24/2 near tip of petal; inside—between Naples Yellow, Plate 403 and Naples Yellow, Plate 403/2 from base to about ½ the distance to the tip, with outer half gradually fusing to margin of Tyrian Rose, Plate 24/2.

*Opening.*—Opens up well; is retarded in opening by cold weather.

Bloom:

*Size* (when fully open).—Medium large; from 2½ inches to 3 inches.

*Petalage.*—Double, but stamens not hidden; from 38 to 40 petals; arranged regularly.

*Form.*—Full and globular at first, but becoming open-cupped; petals at first being loosely rolled inward, but later becoming loosely cupped and rolled outward at maturity.

Petals:

*Texture.*—Thick; leathery.

*Appearance.*—Inside—velvety. Outside—satiny.

*Shape.*—Outside—oval; scalloped; apex having 2 notches. Intermediate—oval; with small spear-like deltoid protruding outward. Inside—obovate; irregularly scalloped.

As observed in both the newly opened and three-days opened flowers grown in a green house at Carlton, Oregon, the bi-color bud coloration remains consistent throughout all petals from the inner petals to the outer petals, except that in the case of the general color effect of the three-days opened flowers, the bi-color changes from white and deep pink to white and light red, with the red coloration being only slightly darker than in the newly opened flowers.

*Behavior.*—Persists; highly resistant to ordinary temperature ranges.

*Flower longevity.*—On bush in garden—6 days in September. Cut roses grown outdoors and kept at living-room temperatures—8 days in September. Cut roses grown in greenhouse and kept at living-room temperatures—8 days in September.

*Reproductive Organs*

Stamens: Medium number, irregularly arranged about pistils. Color—Apricot, Plate 609.

Filaments: Medium long; most with anthers. Color—Primrose Yellow, Plate 601/1.

Anthers: Medium size; open at various times. Color—Apricot, Plate 609.

Pollen: Moderate abundance. Color—gold.

Pistils: Medium number.

Styles: Even; medium long; heavy; bunched.

Stigma: Color—Primrose Yellow, Plate 601/2.

Ovaries: All enclosed in calyx.

Hips: Globular; smooth; walls thick and fleshy. Color—reddish.

Sepals: Falling soon; long; spear-shaped. Color—Scheele's Green, Plate 860.

Seeds: Many; medium size.

*Plant*

Foliage:

*Leaves.*—Compound of 7 leaflets; medium large; heavy; leathery; shiny; thick.

*Leaflets.*—Shape—Lanceolate, with apex acute. Base—acute. Margin—serrate.

*Color.*—Mature: upper surface—moderately dark green; under surface—normal green. Young: upper surface—moderately dark green; under surface—normal green.

*Rachis (the supporting stem of the compound leaf).*—Heavy. Upper side—smooth. Under side—moderately thorny.

*Stipules.*—Long; narrow; with long points turning out at an angle of more than 45°.

*Disease and insect resistance.*—Good resistance to mildew and to aphids (apparently attributable at least in part to shiny and waxy leaf surface), as determined by comparison with other varieties grown in greenhouses at Hillsboro, Oregon, and outdoors at Carlton, Oregon, under same cultural conditions.

Growth:

*Habit.*—Upright; much branched.

*Growth.*—Vigorous.

*Canes.*—Heavy.

*Main stems.*—Color—bright green. Thorns—many; approximately ½ are short and remainder are long; straight; with long, narrow base. Prickles—many; color—green. Hairs—none.

*Branches.*—Color—bright green. Thorns—many short and remainder long; straight; with long, narrow base. Prickles—many; color—green. Hairs—none.

*New shoots.*—Color—pea green, with margins of serrations Crimson, Plate 22/2. Thorns—several; medium long; straight; with long, narrow base. Prickles—few; color—green. Hairs—none.

I claim:

A new and distinct variety of rose plant of the floribunda class, substantially as herein shown and described, characterized particularly as to novely by the unique combination of strong and healthy habits of growth, numerous, upright and strong stems of medium length, large, shiny, thick, luxurious and rich dark green foliage borne on the plant from the ground up to near the flowers, abundant flower production, distinctive and attractive flower buds of buff white color tipped with Crimson over about one-fourth of the outer ends of the petals, said buds gradually opening to present a Crimson irradiance when viewed by looking into the open flowers, and said flowers being of very good quality and having the ability to hold their shape and color for an extended period of time, and a suitability for both commercial cut flower production and for garden decoration.

No reference cited.